(12) United States Patent
Carr

(10) Patent No.: US 12,346,926 B2
(45) Date of Patent: Jul. 1, 2025

(54) HEALTH-RELATED PRODUCT DISCOUNT SYSTEM AND METHOD

(71) Applicant: GIVE BACK ENTERPRISES LLC, Washington, DC (US)

(72) Inventor: Kevin Carr, Milford, CT (US)

(73) Assignee: GIVE BACK ENTERPRISES LLC, Washington, DC (US)

( * ) Notice: Subject to any disclaimer, the term of this patent is extended or adjusted under 35 U.S.C. 154(b) by 198 days.

(21) Appl. No.: 17/345,480

(22) Filed: Jun. 11, 2021

(65) Prior Publication Data

US 2021/0390598 A1    Dec. 16, 2021

Related U.S. Application Data

(60) Provisional application No. 63/038,002, filed on Jun. 11, 2020.

(51) Int. Cl.
*G06Q 30/00* (2023.01)
*G06F 16/29* (2019.01)
(Continued)

(52) U.S. Cl.
CPC ......... *G06Q 30/0222* (2013.01); *G06F 16/29* (2019.01); *G06F 16/9535* (2019.01);
(Continued)

(58) Field of Classification Search
CPC ........... G06Q 30/0222; G06Q 30/0279; G06Q 30/0605; G06Q 30/0625; G06Q 30/0635;
(Continued)

(56) References Cited

U.S. PATENT DOCUMENTS 8,010,380 B2 * 8/2011 Kanaan ............... G06F 16/9537
705/2
10,733,266 B2 * 8/2020 Whitehurst ........... G06Q 10/10
(Continued)

FOREIGN PATENT DOCUMENTS

WO    WO-2018022969 A1 *  2/2018  ......... G06F 19/3475
WO    2021252840 A1     12/2021
(Continued)

OTHER PUBLICATIONS

P. W. Falke and V. S. Mahalle, "Secure spatial Top-k query processing via untrusted location based services accessing outsourced databases," 2017 International Conference on Innovations in Information, Embedded and Communication Sys (ICIIECS), Coimbatore, India, 2017, pp. 1-6, doi: 10.1109/ICIIECS. (Year: 2017).*
(Continued)

*Primary Examiner* — Sun M Li
(74) *Attorney, Agent, or Firm* — Brian J. Colandreo; Heath M. Sargeant; Holland & Knight LLP

(57) ABSTRACT

A computer-implemented method, computer program product and computing system for receiving a query for a health-related product from a user; processing the query to identify providers from which the health-related product may be purchased; and rendering a multi-item result set for the user, wherein each item in the multi-item result set is associated with a provider name, a health-related product cost and a geographic proximity between the user and the provider.

18 Claims, 10 Drawing Sheets

(51) Int. Cl.

| | |
|---|---|
| *G06F 16/9535* | (2019.01) |
| *G06F 16/9537* | (2019.01) |
| *G06Q 30/0207* | (2023.01) |
| *G06Q 30/0279* | (2023.01) |
| *G06Q 30/0601* | (2023.01) |
| *G06Q 40/12* | (2023.01) |
| *G16H 40/20* | (2018.01) |
| *G16H 20/10* | (2018.01) |

(52) U.S. Cl.
CPC ..... *G06F 16/9537* (2019.01); *G06Q 30/0279* (2013.01); *G06Q 30/0605* (2013.01); *G06Q 30/0625* (2013.01); *G06Q 30/0635* (2013.01); *G06Q 30/0639* (2013.01); *G06Q 40/12* (2013.12); *G16H 40/20* (2018.01); *G16H 20/10* (2018.01)

(58) Field of Classification Search
CPC . G06Q 30/0639; G06F 16/29; G06F 16/9535; G06F 16/9537; G16H 40/20; G16H 20/10
See application file for complete search history.

(56) References Cited

U.S. PATENT DOCUMENTS

| | | | |
|---|---|---|---|
| 2002/0120539 A1 | 8/2002 | Price | |
| 2006/0259424 A1 | 11/2006 | Turcotte et al. | |
| 2007/0061245 A1* | 3/2007 | Ramer | G06Q 30/02 705/37 |
| 2008/0015892 A1* | 1/2008 | Gowdy | G06Q 40/04 705/2 |
| 2008/0059227 A1* | 3/2008 | Clapp | G16H 40/67 600/301 |
| 2010/0049652 A1 | 2/2010 | Young | |
| 2011/0173019 A1 | 7/2011 | Benja-Athon | |
| 2012/0259657 A1* | 10/2012 | Keynan | G16Z 99/00 705/2 |
| 2014/0214590 A1* | 7/2014 | Argue | G06Q 30/0631 705/26.7 |
| 2015/0221001 A1 | 8/2015 | Kircher et al. | |
| 2015/0254754 A1* | 9/2015 | Lang | G06Q 40/08 705/4 |
| 2015/0356639 A1* | 12/2015 | Sobhani | G06Q 30/0635 705/39 |
| 2015/0356663 A1* | 12/2015 | Ketchel, III | G16H 70/20 705/2 |
| 2016/0012465 A1* | 1/2016 | Sharp | G06Q 20/321 705/14.17 |
| 2017/0024780 A1* | 1/2017 | Sobhani | G06Q 30/0207 |
| 2017/0148003 A1* | 5/2017 | Lopez | G06Q 30/0279 |
| 2018/0233219 A1* | 8/2018 | Cathcart | G06Q 40/08 |
| 2018/0349484 A1* | 12/2018 | Carlisle | G06F 16/9535 |
| 2019/0378431 A1* | 12/2019 | Ekambaram | G16H 10/60 |
| 2020/0105392 A1* | 4/2020 | Karkazis | G16H 50/30 |
| 2021/0042724 A1* | 2/2021 | Rathod | G07G 1/0054 |

FOREIGN PATENT DOCUMENTS

| | | |
|---|---|---|
| WO | 2021252846 A1 | 12/2021 |
| WO | 2021252857 A1 | 12/2021 |

OTHER PUBLICATIONS

P. W. Falke and V. S. Mahalle, "Secure ranked query processing in location based services accessing outsourced spatial databases," 2017 International Conference on Inventive Systems and Control (ICISC), Coimbatore, India, 2017, pp. 1-6, doi: 10.1109/ICISC.2017.8068580. (Year: 2017).*

M. Abinaya and R. Ganesan, "Effective search mechanism for finding nearest healthcare facilities," 2015 Global Conference on Communication Technologies (GCCT), Thuckalay, India, 2015, pp. 534-538, doi: 10.1109/GCCT.2015.7342719. (Year: 2015).*

Arindam Dasgupta, "A framework for mobile based geospatial public health management," 2010 IEEE Students Technology Symposium (TechSym), Kharagpur, India, 2010, pp. 82-87, doi: 10.1109/TechSym.2010.5469202. (Year: 2010).*

B. Falchuk, "Visual and interaction design themes in mobile healthcare," 2009 6th Annual International Mobile and Ubiquitous Systems: Networking & Services, MobiQuitous, Toronto, ON, Canada, 2009, pp. 1-10, doi: 10.4108/ICST.MobiQuitous2009.6751. (Year: 2009).*

E. B. Sloane, "Using a decision support system tool for healthcare technology assessments," in IEEE Engineering in Medicine and Biology Magazine, vol. 23, No. 3, pp. 42-55, May-Jun. 2004, doi: 10.1109/MEMB.2004.1317981. (Year: 2004).*

I. Ahmad et al., "Current technologies and location based services," 2017 Internet Technologies and Applications (ITA), Wrexham, UK, 2017, pp. 299-304, doi: 10.1109/ITECHA.2017.8101958. (Year: 2017).*

N. Sultanum, D. Singh, M. Brudno and F. Chevalier, "Doccurate: A Curation-Based Approach for Clinical Text Visualization," in IEEE Transactions on Visualization and Computer Graphics, vol. 25, No. 1, pp. 142-151, Jan. 2019, doi: 10.1109/TVCG.2018.2864905 (Year: 2019).*

B. Falchuk, "Visual and interaction design themes in mobile healthcare," 2009 6th Annual International Mobile and Ubiquitous Systems: Networking & Services, MobiQuitous, Toronto, ON, Canada, 2009, pp. 1-10, doi: 10.4108/ICST.MobiQuitous2009.6751. (Year: 2009) (Year: 2009).*

Final Office Action issued in related U.S. Appl. No. 17/345,657 on Aug. 4, 2022.

Final Office Action issued in related U.S. Appl. No. 17/345,569 on Aug. 8, 2022.

Non-Final Office Action issued in related U.S. Appl. No. 17/345,705 on Jun. 1, 2022.

Non-Final Office Action issued in related U.S. Appl. No. 17/345,657 on Oct. 28, 2021.

International Search Report and Written Opinion issued on Sep. 15, 2021 in related Application Serial No. PCT/US2021/036930.

International Search Report and Written Opinion issued on Sep. 2, 2021 in related Application Serial No. PCT/US2021/036940.

International Search Report and Written Opinion issued on Sep. 2, 2021 in related Application Serial No. PCT/US2021/036946.

International Search Report and Written Opinion issued on Sep. 17, 2021 in related Application Serial No. PCT/US2021/03695.

Non-Final Office Action issued in related U.S. Appl. No. 17/345,657 on Mar. 30, 2023.

Non-Final Office Action issued in related U.S. Appl. No. 17/345,569 on May 15, 2023.

Non-Final Office Action issued in related U.S. Appl. No. 17/345,569 on Oct. 29, 2021.

* cited by examiner

SERTRALINE (SER tra leen) is used to treat depression. It may also be used to treat obsessive compulsive disorder, panic disorder, post-trauma stress, premenstrual dysphoric disorder (PMDD) or social anxiety.

(200)

Coupons  202

Basics and Use    Side Effects    Images

Basics and Use

Administration

Take this medicine by mouth with a glass of water. Follow the directions on the prescription label. You can take it with or without food. Take your medicine at regular intervals. Do not take your medicine more often than directed. Do not stop taking this medicine suddenly except upon the advice of your doctor. Stopping this medicine too quickly may cause serious side effects or your condition may worsen.

A special MedGuide will be given to you by the pharmacist with each prescription and refill. Be sure to read this information carefully each time.

Talk to your pediatrician regarding the use of this medicine in children. While this drug may be prescribed for children as young as 7 years for selected conditions, precautions do apply.

Drug Class

Selective Serotonin Reuptake Inhibitor Antidepressants, SSRIs;Selective Serotonin Reuptake Inhibitor Antidepressants, SSRIs;Selective Serotonin Reuptake Inhibitor Antidepressants, SSRIs

Availability

Prescription only

Physical Descriptors green
biconvex
oblong-shaped
scored
side 1;L U
side 2;001

Storage

Keep out of the reach of children.

Store at room temperature between 15 and 30 degrees C (59 and 86 degrees F). Throw away any unused medicine after the expiration date.

Missed Dosage Instructions

If you miss a dose, take it as soon as you can. If it is almost time for your next dose, take only that dose. Do not take double or extra doses.

HEALTH-RELATED PRODUCT DISCOUNT SYSTEM AND METHOD

RELATED APPLICATION(S)

This application claims the benefit of U.S. Provisional Application No. 63/038,002, filed on 11 Jun. 2020, the entire contents of which are herein incorporated by reference.

TECHNICAL FIELD

This disclosure relates to discount systems and, more particularly, to health-related product discount systems.

BACKGROUND

In the world of online shopping, the consuming public has grown accustomed to being able to easily comparison shop. Gone are the days of driving from store to store to compare prices, as this may be easily accomplished today while sitting at your computer in the comfort of your home.

However, people are often looking for more than just good prices when deciding where to spend their money. Specifically, people often look to see how their purchase may serve the greater good, such as benefitting target organizations (e.g., charities) that serve a particular area that they are interested in. Unfortunately and with respect to the purchase of health-related product, the ability to comparison shop while serving the greater good is compromised.

SUMMARY OF DISCLOSURE

Concept #1

In one implementation, a computer-implemented method is executed on a computing device and includes: receiving a query for a health-related product from a user; processing the query to identify providers from which the health-related product may be purchased; and rendering a multi-item result set for the user, wherein each item in the multi-item result set is associated with a provider name, a health-related product cost and a geographic proximity between the user and the provider.

One or more of the following features may be included. A geographic location may be defined of the user. A map may be rendered that visually locates each provider defined within the multi-item result set with respect to the geographic location of the user. Health-related product information may be provided to the user concerning the health-related product defined within the query. The user may be enabled to sort the multi-item result set based upon one or more of the provider name, the health-related product cost and the geographic proximity between the user and the provider. The user may be enabled to obtain a coupon to purchase the health-related product from a selected provider defined within the multi-item result set for the health-related product cost associated with the selected provider. Rendering a multi-item result set for the user may include: rendering indicia that identifies one or more items within the multi-item result set that have the lowest health-related product cost. Rendering a multi-item result set for the user may include: rendering indicia that identifies one or more items within the multi-item result set that have the best health-related product costs. Rendering a multi-item result set for the user may include: presorting the items within the multi-item result set based upon geographic proximity between the user and the provider. Rendering a multi-item result set for the user may include: enabling the user to refine the multi-item result set based upon one or more of: a health-related product name; a health-related product form; a health-related product dosage; and a health-related product quantity.

In another implementation, a computer program product resides on a computer readable medium and has a plurality of instructions stored on it. When executed by a processor, the instructions cause the processor to perform operations including: receiving a query for a health-related product from a user; processing the query to identify providers from which the health-related product may be purchased; and rendering a multi-item result set for the user, wherein each item in the multi-item result set is associated with a provider name, a health-related product cost and a geographic proximity between the user and the provider.

One or more of the following features may be included. A geographic location may be defined of the user. A map may be rendered that visually locates each provider defined within the multi-item result set with respect to the geographic location of the user. Health-related product information may be provided to the user concerning the health-related product defined within the query. The user may be enabled to sort the multi-item result set based upon one or more of the provider name, the health-related product cost and the geographic proximity between the user and the provider. The user may be enabled to obtain a coupon to purchase the health-related product from a selected provider defined within the multi-item result set for the health-related product cost associated with the selected provider. Rendering a multi-item result set for the user may include: rendering indicia that identifies one or more items within the multi-item result set that have the lowest health-related product cost. Rendering a multi-item result set for the user may include: rendering indicia that identifies one or more items within the multi-item result set that have the best health-related product costs. Rendering a multi-item result set for the user may include: presorting the items within the multi-item result set based upon geographic proximity between the user and the provider. Rendering a multi-item result set for the user may include: enabling the user to refine the multi-item result set based upon one or more of: a health-related product name; a health-related product form; a health-related product dosage; and a health-related product quantity.

In another implementation, a computing system includes a processor and memory is configured to perform operations including: receiving a query for a health-related product from a user; processing the query to identify providers from which the health-related product may be purchased; and rendering a multi-item result set for the user, wherein each item in the multi-item result set is associated with a provider name, a health-related product cost and a geographic proximity between the user and the provider.

One or more of the following features may be included. A geographic location may be defined of the user. A map may be rendered that visually locates each provider defined within the multi-item result set with respect to the geographic location of the user. Health-related product information may be provided to the user concerning the health-related product defined within the query. The user may be enabled to sort the multi-item result set based upon one or more of the provider name, the health-related product cost and the geographic proximity between the user and the provider. The user may be enabled to obtain a coupon to purchase the health-related product from a selected provider defined within the multi-item result set for the mediation cost associated with the selected provider. Rendering a multi-item result set for the user may include: rendering indicia that identifies one or more items within the multi-item result set that have the lowest health-related product cost. Rendering a multi-item result set for the user may include: rendering indicia that identifies one or more items within the multi-item result set that have the best health-related product costs. Rendering a multi-item result set for the user may include: presorting the items within the multi-item result set based upon geographic proximity between the user and the provider. Rendering a multi-item result set for the user may include: enabling the user to refine the multi-item result set based upon one or more of: a health-related product name; a health-related product form; a health-related product dosage; and a health-related product quantity.

The details of one or more implementations are set forth in the accompanying drawings and the description below. Other features and advantages will become apparent from the description, the drawings, and the claims.

BRIEF DESCRIPTION OF THE DRAWINGS

FIGS. 3-6 are diagrammatic views of a web-based user interface rendered by the health-related product discount process of FIG. 1 according to an embodiment of the present disclosure;

Like reference symbols in the various drawings indicate like elements.

DETAILED DESCRIPTION OF THE PREFERRED EMBODIMENTS

System Overview

Figure 1:
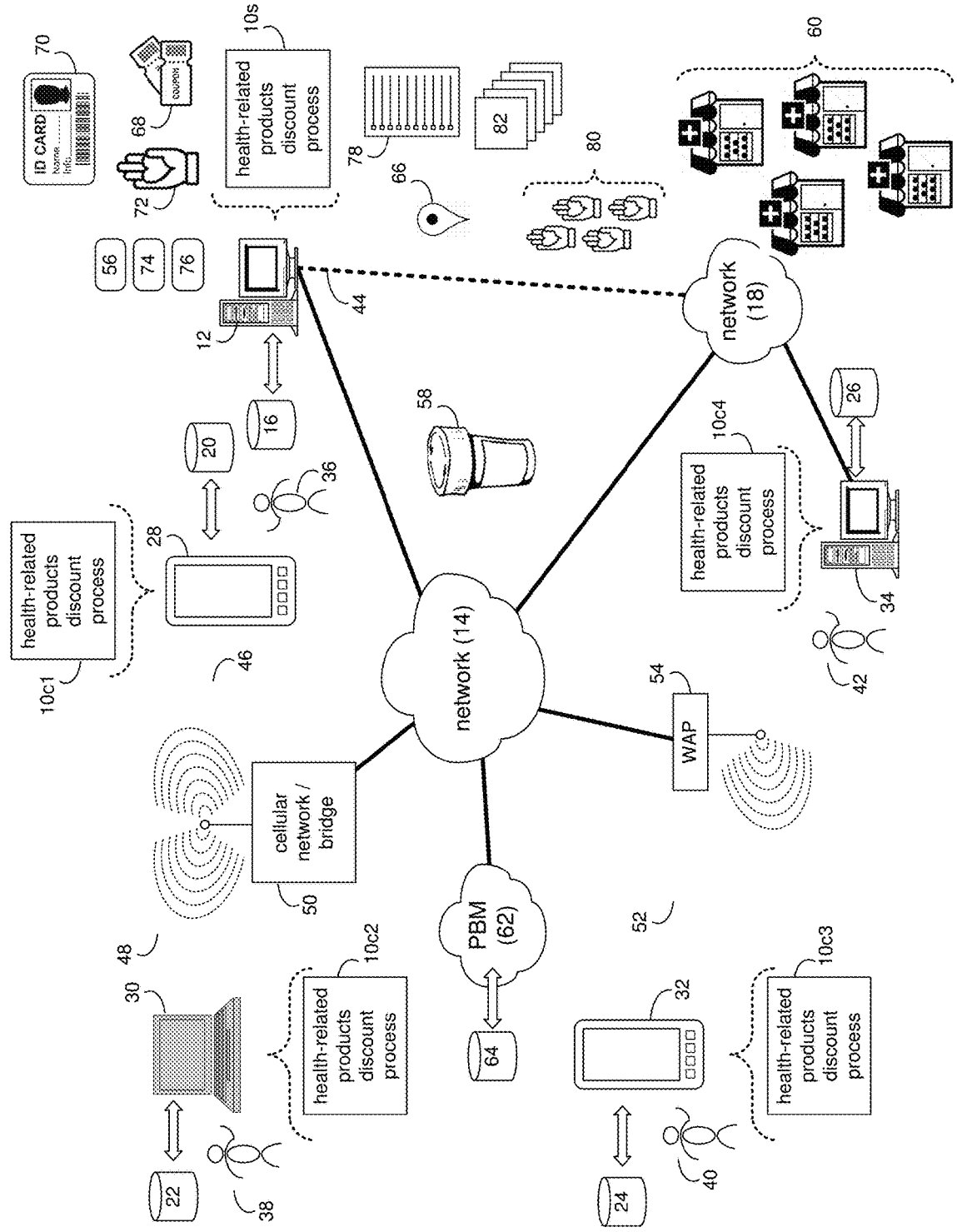
FIG. 1 is a diagrammatic view of a distributed computing network including a computing device that executes a health-related product discount process according to an embodiment of the present disclosure.

Referring to FIG. 1, there is shown health-related product discount process 10. Health-related product discount process 10 may be implemented as a server-side process, a client-side process, or a hybrid server-side/client-side process. For example, health-related product discount process 10 may be implemented as a purely server-side process via health-related product discount process 10s. Alternatively, health-related product discount process 10 may be implemented as a purely client-side process via one or more of health-related product discount process 10c1, health-related product discount process 10c2, health-related product discount process 10c3, and health-related product discount process 10c4. Alternatively still, health-related product discount process 10 may be implemented as a hybrid server-side/client-side process via health-related product discount process 10s in combination with one or more of health-related product discount process 10c1, health-related product discount process 10c2, health-related product discount process 10c3, and health-related product discount process 10c4. Accordingly, health-related product discount process 10 as used in this disclosure may include any combination of health-related product discount process 10s, health-related product discount process 10c1, health-related product discount process 10c2, health-related product discount process 10c3, and health-related product discount process 10c4.

Health-related product discount process 10s may be a server application and may reside on and may be executed by computing device 12, which may be connected to network 14 (e.g., the Internet or a local area network). Examples of computing device 12 may include, but are not limited to: a personal computer, a laptop computer, a personal digital assistant, a data-enabled cellular telephone, a notebook computer, a television with one or more processors embedded therein or coupled thereto, a cable/satellite receiver with one or more processors embedded therein or coupled thereto, a server computer, a series of server computers, a mini computer, a mainframe computer, or a cloud-based computing network.

The instruction sets and subroutines of health-related product discount process 10s, which may be stored on storage device 16 coupled to computing device 12, may be executed by one or more processors (not shown) and one or more memory architectures (not shown) included within computing device 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Examples of health-related product discount processes 10c1, 10c2, 10c3, 10c4 may include but are not limited to a client application, a web browser, a game console user interface, or a specialized application (e.g., an application running on e.g., the Android™ platform or the iOS™ platform). The instruction sets and subroutines of health-related product discount processes 10c1, 10c2, 10c3, 10c4, which may be stored on storage devices 20, 22, 24, 26 (respectively) coupled to client electronic devices 28, 30, 32, 34 (respectively), may be executed by one or more processors (not shown) and one or more memory architectures (not shown) incorporated into client electronic devices 28, 30, 32, 34 (respectively). Examples of storage devices 20, 22, 24, 26 may include but are not limited to: a hard disk drive; a RAID device; a random access memory (RAM); a read-only memory (ROM); and all forms of flash memory storage devices.

Examples of client electronic devices 28, 30, 32, 34 may include, but are not limited to, data-enabled, cellular telephone 28, laptop computer 30, personal digital assistant 32, personal computer 34, a notebook computer (not shown), a server computer (not shown), a gaming console (not shown), a smart television (not shown), and a dedicated network device (not shown). Client electronic devices 28, 30, 32, 34 may each execute an operating system, examples of which may include but are not limited to Microsoft Windows™, Android™, WebOS™, iOS™, Redhat Linux™, or a custom operating system.

Users 36, 38, 40, 42 may access health-related product discount process 10 directly through network 14 or through secondary network 18. Further, health-related product discount process 10 may be connected to network 14 through secondary network 18, as illustrated with link line 44.

The various client electronic devices (e.g., client electronic devices 28, 30, 32, 34) may be directly or indirectly coupled to network 14 (or network 18). For example, data-enabled, cellular telephone 28 and laptop computer 30 are shown wirelessly coupled to network 14 via wireless communication channels 46, 48 (respectively) established between data-enabled, cellular telephone 28, laptop computer 30 (respectively) and cellular network/bridge 50, which is shown directly coupled to network 14. Further, personal digital assistant 32 is shown wirelessly coupled to network 14 via wireless communication channel 52 established between personal digital assistant 32 and wireless access point (i.e., WAP) 54, which is shown directly coupled to network 14. Additionally, personal computer 34 is shown directly coupled to network 18 via a hardwired network connection.

WAP 54 may be, for example, an IEEE 802.11a, 802.11b, 802.11g, 802.11n, Wi-Fi, and/or Bluetooth device that is capable of establishing wireless communication channel 52 between personal digital assistant 32 and WAP 54. As is known in the art, IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth is a telecommunications industry specification that allows e.g., mobile phones, computers, and personal digital assistants to be interconnected using a short-range wireless connection.

Health-Related Product Discount Process

As will be discussed below in greater detail, health-related product discount process 10 may be configured to enable a user (e.g., one or more of users 36, 38, 40, 42) to search for a particular health-related product (e.g., prescription medication, over-the-counter medication, diabetes test strips, pregnancy tests, blood glucose meters, syringes, vitamins, and healthcare products) to determine which providers sell the health-related product, how much the providers charge for the health-related product, and the location of the providers with respect to the user (e.g., one or more of users 36, 38, 40, 42).

Concept #1

Figure 2:
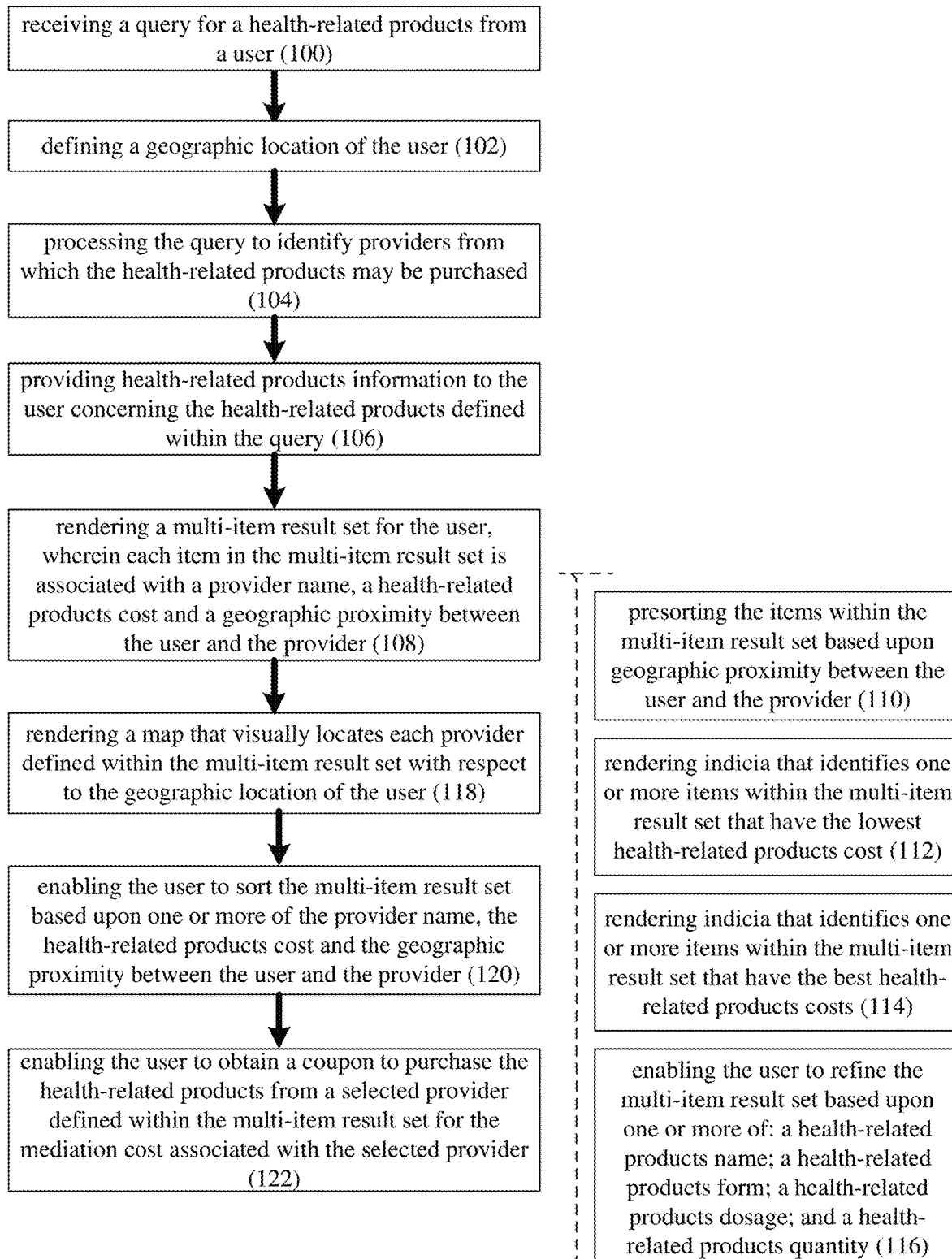
FIG. 2 is a flowchart of an implementation of the health-related product discount process of FIG. 1 according to an embodiment of the present disclosure.
Figure 3:
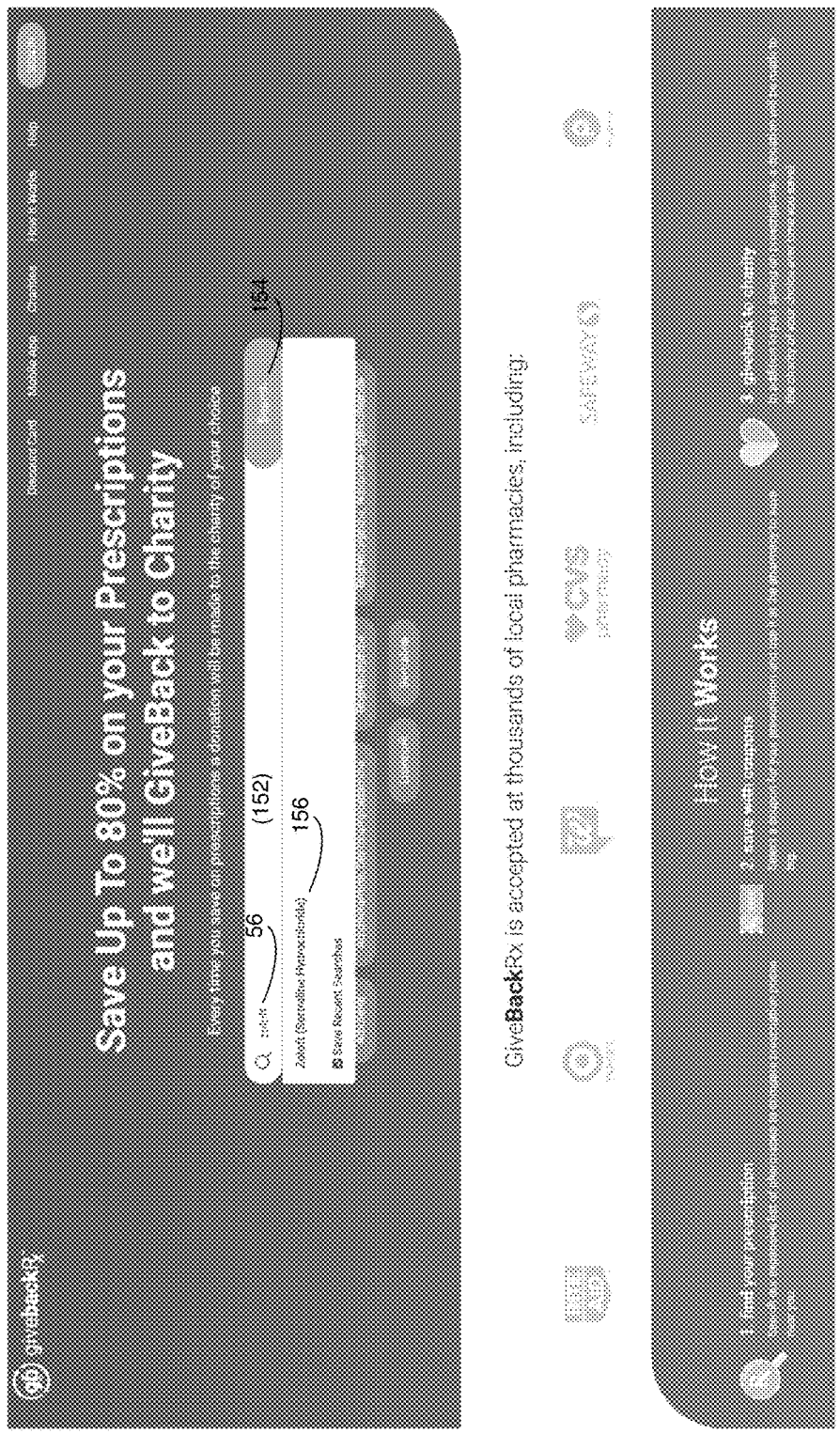

Referring also to FIG. 2-3, health-related product discount process 10 may receive 100 a query (e.g., query 56) for a health-related product (e.g., health-related product 58) from a user (e.g., user 36). For example, assume that user 36 has a prescription for Zoloft that they need to have filled . . . but they do not know where they can have it filled locally and/or where they will get the best price.

Accordingly, health-related product discount process 10 may render user interface 150 that may allow user 36 to define query 56 within query field 152. Specifically, user 36 may type "zoloft" into query field 152 and select "Search" button 154, thus defining query 56. As user 36 types the name of the health-related product (e.g., health-related product 58) that they are searching for, health-related product discount process 10 may render suggestions in suggestion field 156.

Health-related product discount process 10 may define 102 a geographic location (e.g., geographic location 66) of the user (e.g., user 36). Geographic location 66 may be defined in various ways. For example and if using a handheld device with a GPS chipset (e.g., data-enabled, cellular telephone 28), health-related product discount process 10 may access this GPS chipset to define 102 geographic location 66. Additionally/alternatively, health-related product discount process 10 may request that the user (e.g., user 36) manually define their geographic location (e.g., geographic location 66).

Health-related product discount process 10 may process 104 the query (e.g., query 56) to identify providers (e.g., providers 60) from which the health-related product (e.g., health-related product 58) may be purchased. Specifically, health-related product discount process 10 may be configured to interact with/work with a pharmacy benefit manager (e.g., PBM 62). In the United States, a pharmacy benefit manager (PBM) is a third-party administrator of prescription drug programs for commercial health plans, self-insured employer plans, Medicare Part D plans, the Federal Employees Health Benefits Program, and state government employee plans. According to the American Pharmacists Association, "PBMs are primarily responsible for developing and maintaining the formulary, contracting with pharmacies, negotiating discounts and rebates with drug manufacturers, and processing and paying prescription drug claims." PBMs operate inside of integrated healthcare systems (e.g., Kaiser Permanente or Veterans Health Administration), as part of retail pharmacies (e.g., CVS Pharmacy or Rite-Aid), and as part of insurance companies (e.g., UnitedHealth Group). Accordingly, PBM 62 may be knowledgeable of the prices that the providers (e.g., providers 60) charge for various health-related products (e.g., health-related product 58) as well as the physical locations of the providers (e.g., providers 60), wherein this medicine cost information and provider location information may be stored within database 64 accessible by/coupled to PBM 62.

Referring also to FIG. 4 and once health-related product discount process 10 processes 104 the query (e.g., query 56), health-related product discount process 10 may provide 106 health-related product information (e.g., health-related product information 200) to the user (e.g., user 36) concerning the health-related product (e.g., health-related product 58) defined within the query (e.g., query 56). For example and if such health-related product information (e.g., health-related product information 200) is desired, the user (e.g., user 36) may select information button 202, which may result in health-related product discount process 10 providing 106 health-related product information 200.

Figure 5:
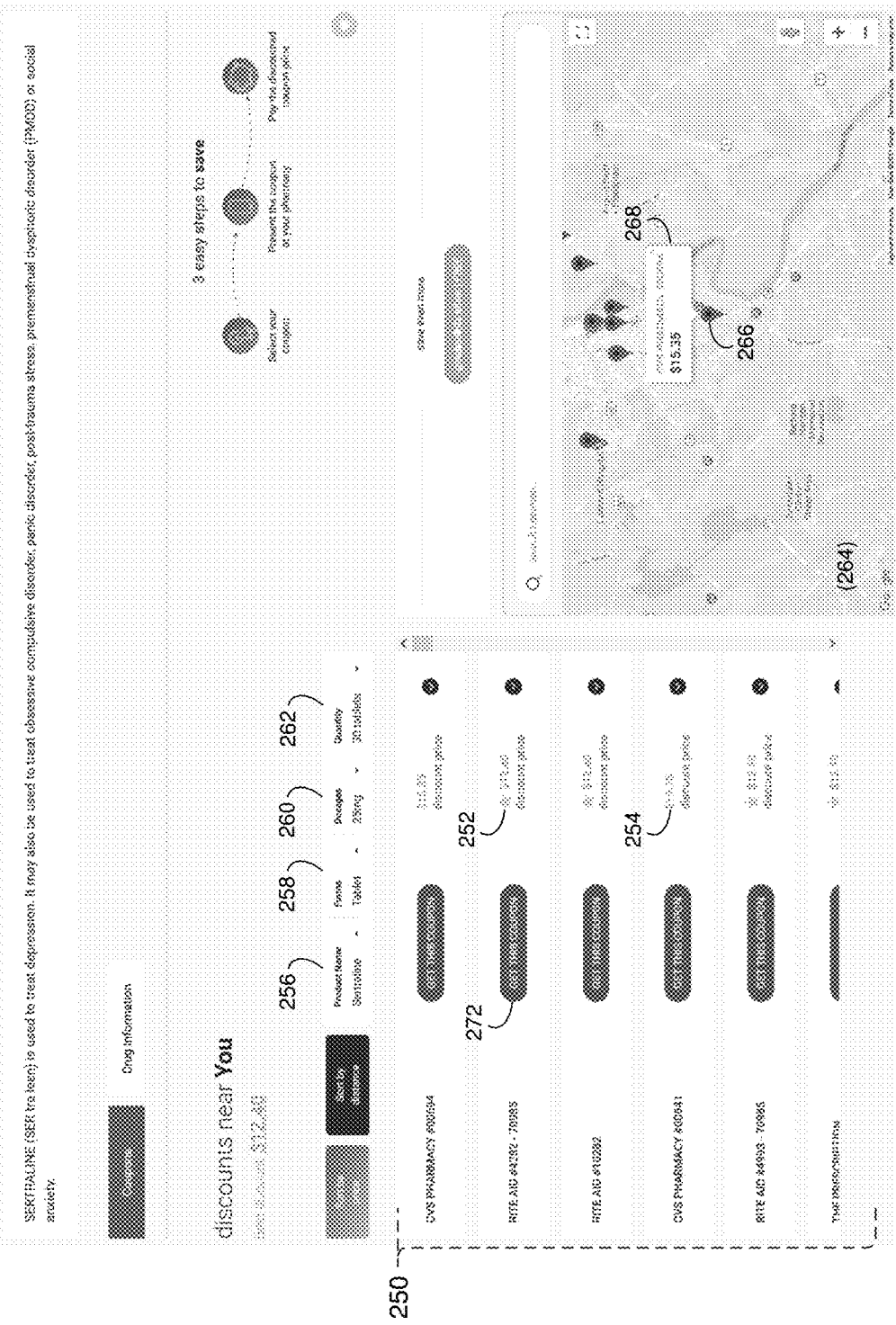

Referring also to FIG. 5 and once health-related product discount process 10 processes 104 the query (e.g., query 56), health-related product discount process 10 may render 108 a multi-item result set (e.g., multi-item result set 250) for the user (e.g., user 36), wherein each item in the multi-item result set (e.g., multi-item result set 250) may be associated with a provider name, a health-related product cost and a geographic proximity between the user (e.g., user 36) and the provider.

When rendering 108 a multi-item result set (e.g., multi-item result set 250) for the user (e.g., user 36), health-related product discount process 10 may presort 110 the items within the multi-item result set (e.g., multi-item result set 250) based upon geographic proximity between the user (e.g., user 36) and the provider. For example and with respect to multi-item result set 250, the provider closest to user 36 is "CVS PHARMACY #00694" (with a health-related product cost of $15.35), wherein the provider second closest to user 36 is "RITE AID #4282-70985" (with a health-related product cost of $12.40), wherein the provider third closest to user 36 is "RITE AID #10282" (with a health-related product cost of $12.40), and so on. Accordingly and if convenience is of primary importance to user 36, user 36 may be able to determine the closest provider of health-related product 58 (i.e., is "CVS PHARMACY #00694") regardless of cost considerations.

When rendering 108 a multi-item result set (e.g., multi-item result set 250) for the user (e.g., user 36), health-related product discount process 10 may render 112 indicia that identifies one or more items within the multi-item result set (e.g., multi-item result set 250) that have the lowest health-related product cost. For example, health-related product discount process 10 may render 112 indicia (e.g., star 252) next to the lowest health-related product cost for which the health-related product (e.g., health-related product 58) is available. Accordingly, if $12.40 is the lowest health-related product cost and four providers charge that amount for health-related product 58, each item within multi-item result set 250 that has a health-related product cost of $12.40 will have a star (e.g., star 252) next to it, thus indicating that this is the lowest health-related product cost within multi-item result set 250.

Additionally and when rendering 108 a multi-item result set (e.g., multi-item result set 250) for the user (e.g., user 36), health-related product discount process 10 may render 114 indicia that identifies one or more items within the multi-item result set (e.g., multi-item result set 250) that have the best health-related product costs. For example, health-related product discount process 10 may render 114 indicia (e.g., green text 254) for the best health-related product costs for which the health-related product (e.g., health-related product 58) is available. For example, assume that green text (e.g., green text 254) indicates the ten providers that have the best health-related product costs. As discussed above, $12.40 is the lowest health-related product cost and four providers charge that amount for health-related product 58. Accordingly, the four providers that charge $12.40 will include green text (e.g., green text 254). Further, the next six providers that have the best health-related product costs will also be identified with green text (e.g., green text 254), resulting in the ten providers that have the best health-related product costs being identified with green text (e.g., green text 254).

When rendering 108 a multi-item result set (e.g., multi-item result set 250) for the user (e.g., user 36), health-related product discount process 10 may enable 116 the user (e.g., user 36) to refine the multi-item result set (e.g., multi-item result set 250) based upon one or more of: a health-related product name; a health-related product form; a health-related product dosage; and a health-related product quantity.

Health-Related Product Name; Name field 256 may enable user 36 to select a specific brand for health-related product 58. For example, if health-related product 58 was a type of health-related product (e.g., Ibuprofen), name field 256 may enable user 36 to select a specific brand of that health-related product type.

Health-Related Product Form; Form field 258 may enable user 36 to select a specific form for health-related product 58. For example, if health-related product 58 is available as a tablet, a capsule and drops, form field 256 may enable user 36 to select a specific form of that health-related product type.

Health-Related Product Dosage; Dosage field 260 may enable user 36 to select a specific dosage for health-related product 58. For example, if health-related product 58 was available in three dosages (e.g., 25 mg, 50 mg and 100 mg), dosage field 260 may enable user 36 to select a specific dosage of that health-related product type.

Health-Related Product Quantity: Quantity field 262 may enable user 36 to select a specific quantity for health-related product 58. For example, if health-related product 58 was available in three quantities (e.g., 30 tablets, 60 tablets, and 120 tablets), quantity field 262 may enable user 36 to select a specific quantity of that health-related product type.

Health-related product discount process 10 may render 118 a map (e.g., map 264) that visually locates each provider defined within the multi-item result set (e.g., multi-item result set 250) with respect to the geographic location of the user (e.g., user 36). As shown within map 264, each provider defined within the multi-item result set (e.g., multi-item result set 250) may be located on the map with a locating pin (e.g., locating pin 266) which (in this example) is associated with the provider closest to user 36 (i.e., "CVS PHARMACY #00694" having a health-related product cost of $15.35 as defined within locating pin window 268). In the event that user 36 selects any of the other locating pins, a similar locating pin window will be rendered by health-related product discount process 10.

As discussed above, the multi-item result set (e.g., multi-item result set 250) may be initially sorted (by default) based upon the geographic proximity between user 36 and each of the providers defined within the multi-item result set (e.g., multi-item result set 250). However, health-related product discount process 10 may enable 120 the user (e.g., user 36) to sort the multi-item result set (e.g., multi-item result set 250) based upon one or more of the provider name, the health-related product cost and the geographic proximity between the user (e.g., user 36) and the provider.

Figure 6:
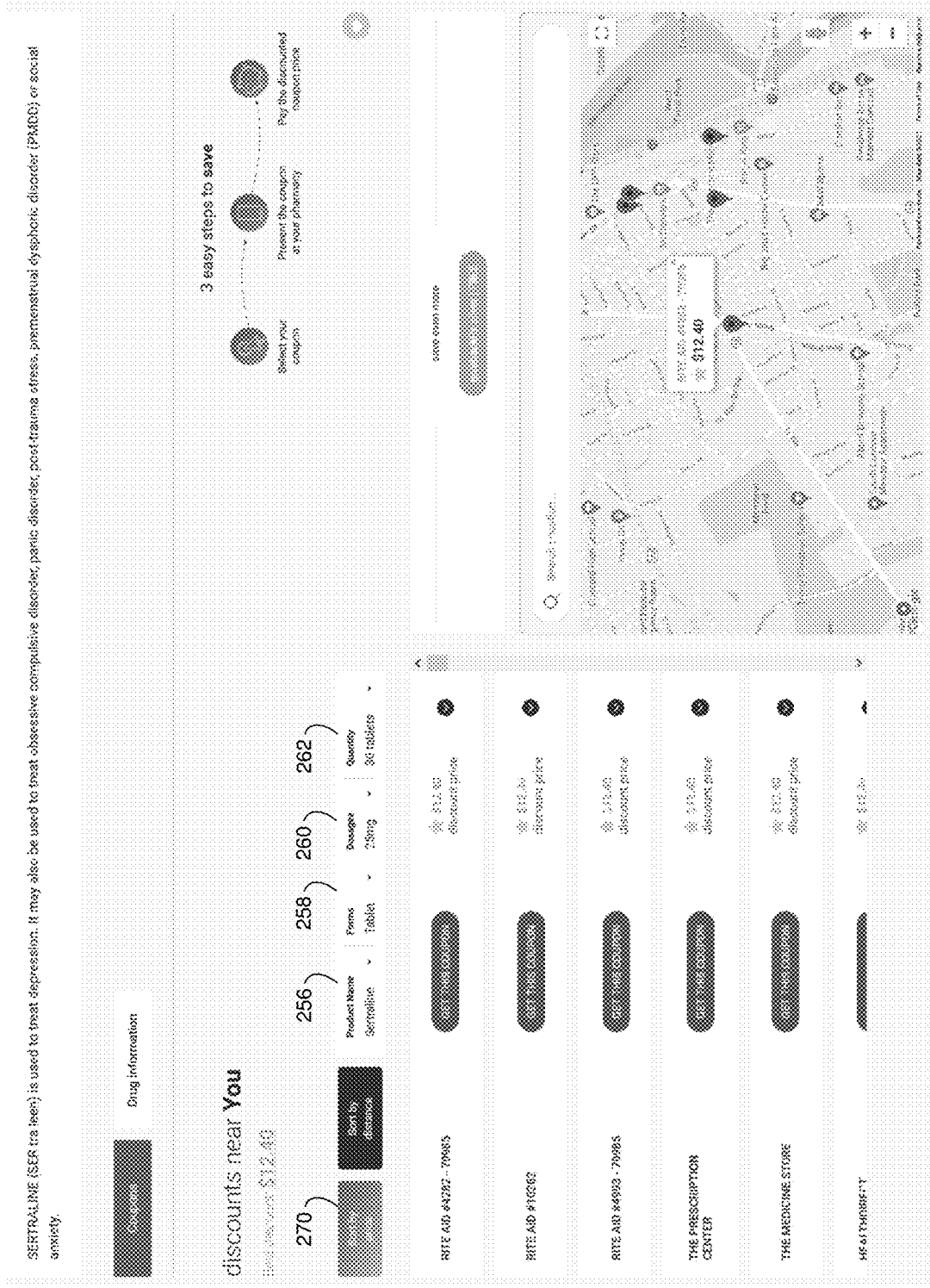

For example and referring also to FIG. 6, if the health-related product cost is of primary consideration for user 36 (regardless of geographic proximity to user 36), health-related product discount process 10 may enable 120 the user (e.g., user 36) to sort the multi-item result set (e.g., multi-item result set 250) based upon the health-related product cost (e.g., by selecting sort button 270). Further, if the name of the provider is of primary consideration for user 36 (regardless of health-related product cost or geographic proximity to user 36), health-related product discount process 10 may enable 120 the user (e.g., user 36) to sort the multi-item result set (e.g., multi-item result set 250) based upon the provider name (e.g., if user 36 really likes Rite Aid pharmacies).

Health-related product discount process 10 may enable 122 the user (e.g., user 36) to obtain a coupon (e.g., coupon 68) to purchase the health-related product (e.g., health-related product 58) from a selected provider defined within the multi-item result set (e.g., multi-item result set 250) for the mediation cost associated with the selected provider. For example, assume that user 36 wishes to purchase health-related product 58 from "RITE AID #4282-70985" (with a health-related product cost of $12.40), user 36 may select "GET THIS COUPON" button 272 and coupon 68 may e.g., be printed or sent to data-enabled, cellular telephone 28 for redemption at "RITE AID #4282-70985". Additionally/alternatively, if user 36 is a member of health-related product discount process 10, user 36 may have a membership card (e.g., membership card 70) that defines various pieces of information (such as a Member ID #, a Group # and a BIN #), wherein membership card 70 may be provided to "RITE AID #4282-70985", thus eliminating the need for user 36 to obtain coupon 68.

Figure 7:
FIG. 7 is a diagrammatic view of an app-based user interface rendered by the health-related product discount process of FIG. 1 according to an embodiment of the present disclosure.

While user interface 150 is discussed above and shown in the related figures as being a web-based user interface, this is for illustrative purposes only and is not intended to be a limitation of this disclosure, as other configurations are possible and are considered to be included within the scope of this disclosure. For example and referring also to FIG. 7, there is shown an application-based user interface (e.g., user interface 150') that is configured to be rendered on an electronic device (e.g., data-enabled, cellular telephone 28).

Concept #2

Figure 8:
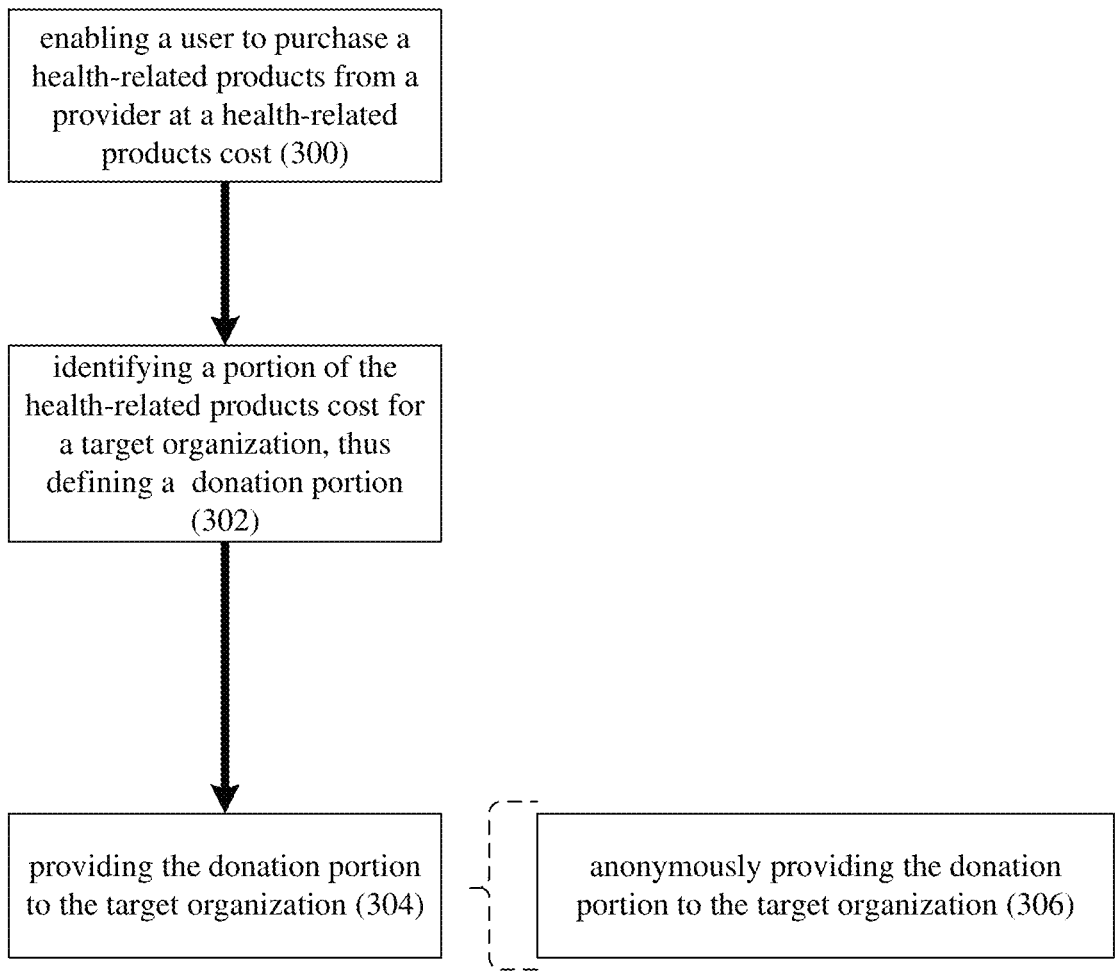
FIG. 8 is a flowchart of an implementation of the health-related product discount process of FIG. 1 according to an embodiment of the present disclosure.

Referring also to FIG. 8, health-related product discount process 10 may enable 300 a user (e.g., user 36) to purchase a health-related product (e.g., health-related product 58) from a provider at a health-related product cost. As discussed above, health-related product discount process 10 may enable 300 user 36 to purchase health-related product 58 from any of the providers defined within multi-item result set (e.g., multi-item result set 250).

Additionally, health-related product discount process 10 may identify 302 a portion of the health-related product cost for a target organization (e.g., target organization 72), thus defining a donation portion (e.g., donation portion 74). An example of target organization 72 may include but is not limited to a charitable organization.

This target organization (e.g., target organization 72) may be a user-defined target organization or a platform-defined, target organization. For example, health-related product discount process 10 may be configured to allow user 36 to select the target organization (e.g., the Wounded Warrior Project) to which the donation portion (e.g., donation portion 74) may be directed. Additionally/alternatively, health-related product discount process 10 may be configured to automatically select a target organization (e.g., Salvation Army) to which the donation portion (e.g., donation portion 74) may be directed. This platform-defined, target organization may be periodically redefined in the form of e.g., a "Charity of the Month", wherein health-related product discount process 10 periodically redefines the target organization to which the donation portion (e.g., donation portion 74) may be directed.

The donation portion (e.g., donation portion 74) may be a fixed amount that is based upon a tier defined for the health-related product (e.g., health-related product 58). For example, health-related products (e.g., health-related product 58) may be divided into various tiers (e.g., Tier 1-Tier 8), wherein the tier into which a health-related product is placed may define the donation portion (e.g., donation portion 74). For example:

Tier 1 Health-Related Products may have a donation portion (e.g., donation portion 74) of $0.25:
Tier 2 Health-Related Products may have a donation portion (e.g., donation portion 74) of $0.50:
Tier 3 Health-Related Products may have a donation portion (e.g., donation portion 74) of $0.75:
Tier 4 Health-Related Products may have a donation portion (e.g., donation portion 74) of $1.00:
Tier 5 Health-Related Products may have a donation portion (e.g., donation portion 74) of $1.25:
Tier 6 Health-Related Products may have a donation portion (e.g., donation portion 74) of $1.50:
Tier 7 Health-Related Products may have a donation portion (e.g., donation portion 74) of $1.75: and
Tier 8 Health-Related Products may have a donation portion (e.g., donation portion 74) of $2.00.

Additionally/alternatively, the donation portion (e.g., donation portion 74) may be a percentage of the health-related product cost. For example, the donation portion (e.g., donation portion 74) may be a fixed percentage (e.g., 1%) of the health-related product cost. Alternatively, the donation portion (e.g., donation portion 74) may be a graduated percentage (e.g., 1% of the first $10, 0.75% of the next $10 and 0.50% of any amount above that).

Health-related product discount process 10 may provide 304 the donation portion (e.g., donation portion 74) to the target organization (e.g., target organization 72). As discussed above, health-related product discount process 10 may be configured to interact with/work with a pharmacy benefit manager (e.g., PBM 62), wherein PBM 62 may be knowledgeable of the prices that the providers (e.g., providers 60) charge for various health-related products (e.g., health-related product 58). Specifically and when e.g., user 36 purchases a health-related product (e.g., health-related product 58), a portion of the cost of health-related product 58 may be provided to PBM 62 (thus defining a PBM portion 76), wherein the donation portion (e.g., donation portion 74) may be a sub-portion of PBM portion 76.

As discussed above, PBMs may contract with pharmacies and negotiate discounts and rebates with drug manufacturers. Accordingly, assume for this example that PBM 62 negotiated a health-related product cost of $20 for Health-related product XYZ when purchased from Pharmacy ABC. For this example, assume that user 36 purchases Health-related product XYZ for a health-related product cost of $20 at Pharmacy ABC. PBM 62 may have negotiated a PBM portion 76 of $2 with respect to purchases of Health-related product XYZ from Pharmacy ABC. Therefore, whenever health-related product discount process 10 is used to purchase Health-related product XYZ from Pharmacy ABC, the user will pay $20 to Pharmacy ABC, wherein Pharmacy ABC keeps $18 of the $20 and provides a PBM portion (e.g., PBM portion 76) of $2 back to PBM 62. As discussed above, the donation portion (e.g., donation portion 74) may be a sub-portion of PBM portion 76. For example, PBM 62 may provide $1 of their $2 PBM portion (e.g., PBM portion 76) to health-related product discount process 10, wherein health-related product discount process 10 may provide 304 a portion of this $1 (e.g., donation portion 74) to the target organization (e.g., target organization 72).

When providing 304 the donation portion (e.g., donation portion 74) to the target organization (e.g., target organization 72), health-related product discount process 10 may anonymously provide 306 the donation portion (e.g., donation portion 74) to the target organization (e.g., target organization 72). For example, health-related product discount process 10 may be configured to allow users (e.g., user 36) to utilize health-related product discount process 10 in different ways. For example, health-related product discount process 10 may allow user 36 to be a registered user, a totally anonymous user or a charity-specific anonymous user.

When user 36 is a Registered User:
User 36 can pick their target organization (e.g., target organization 72).
The donation portion (e.g., donation portion 74) is made to the target organization (e.g., target organization 72) in the name of user 36.

The prescription purchased by user 36 is tied to user 36 within health-related product discount process 10.

When user 36 is a Totally Anonymous User:

User 36 cannot pick their target organization (e.g., target organization 72) and the target organization is picked by health-related product discount process 10 (e.g., "Charity of the Month").

The donation portion (e.g., donation portion 74) is made to the target organization (e.g., target organization 72) anonymously.

The prescription purchased by user 36 is not tied to user 36 within health-related product discount process 10.

When user 36 is a Charity-Specific Anonymous User:

User 36 can pick their target organization (e.g., target organization 72) by picking a card/coupon associated with e.g., target organization 72 (e.g., the Wounded Warrior Project may have a unique member ID and the card/coupon may identify that unique member ID).

The donation portion (e.g., donation portion 74) is made to the target organization (e.g., target organization 72) anonymously.

The prescription purchased by user 36 is not tied to user 36 within health-related product discount process 10.

Concept #3

Figure 9:
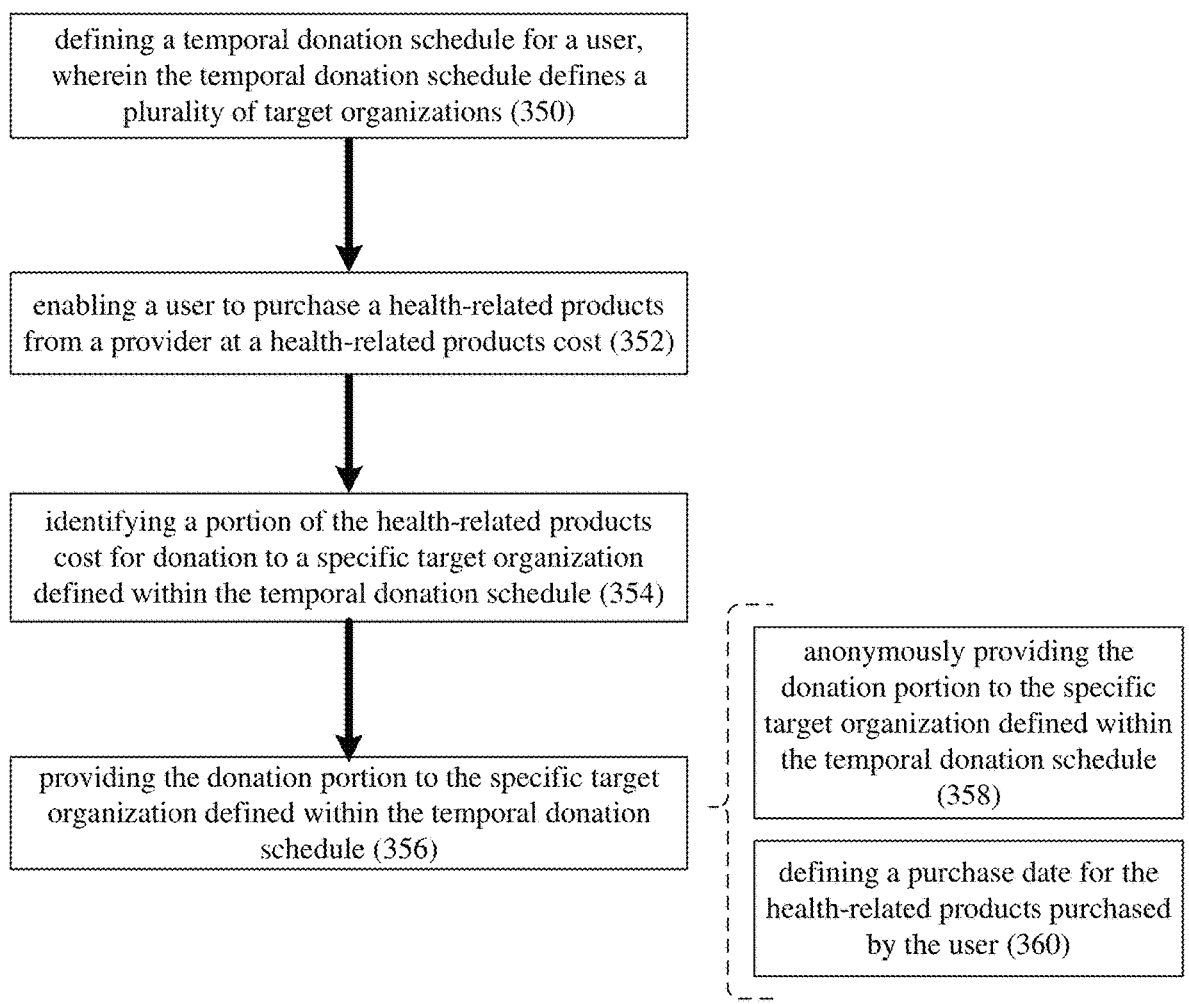
FIG. 9 is a flowchart of an implementation of the health-related product discount process of FIG. 1 according to an embodiment of the present disclosure.

Referring also to FIG. 9, health-related product discount process 10 may define 350 a temporal donation schedule (e.g., temporal donation schedule 78) for a user (e.g., user 36), wherein the temporal donation schedule (e.g., temporal donation schedule 78) may define a plurality of target organizations (e.g., plurality of target organizations 80).

The temporal donation schedule (e.g., temporal donation schedule 78) may define a donation period for each of the plurality of target organizations (e.g., plurality of target organizations 80). For example, assume that user 36 has several charities that they are interested in supporting with donation portion 74, such as the Wounded Warrior Project, St. Jude Children's Research Hospital, Susan G. Komen, and the Salvation Army. Accordingly, user 36 may define a temporal donation schedule (e.g., temporal donation schedule 78) that supports (and directs donation portion 74 to) the Wounded Warrior Project (from 1 January-31 March), St. Jude Children's Research Hospital (from 1 April-30 June), Susan G. Komen (from 1 July-30 September), and the Salvation Army (from 1 October-31 December).

As discussed above, health-related product discount process 10 may enable 352 a user (e.g., user 36) to purchase a health-related product (e.g., health-related product 58) from a provider at a health-related product cost. For example, health-related product discount process 10 may enable 352 user 36 to purchase health-related product 58 from any of the providers (e.g., providers 60) defined within the multi-item result set (e.g., multi-item result set 250).

Health-related product discount process 10 may identify 354 a portion of the health-related product cost for donation to a specific target organization defined within the temporal donation schedule (e.g., temporal donation schedule 78), thus defining a donation portion (e.g., donation portion 74). Health-related product discount process 10 may then provide 356 the donation portion (e.g., donation portion 74) to the specific target organization defined within the temporal donation schedule (e.g., temporal donation schedule 78).

When providing 356 the donation portion (e.g., donation portion 74) to the specific target organization defined within the temporal donation schedule (e.g., temporal donation schedule 78), health-related product discount process 10 may define 360 a purchase date for the health-related product (e.g., health-related product 58) purchased by the user (e.g., user 36), wherein the specific target organization may have a donation period that includes the purchase date. For example, if user 36 purchased Health-related product XYZ from Pharmacy ABC on 27 Apr. 2021, donation portion 74 associated with that purchase will be directed to St. Jude Children's Research Hospital, as 27 April falls within 1 April-30 June.

In the manner described above with respect to user 36 being a registered user, a totally anonymous user or a charity-specific anonymous user, when providing 356 the donation portion (e.g., donation portion 74) to the specific target organization defined within the temporal donation schedule (e.g., temporal donation schedule 78), health-related product discount process 10 may anonymously provide 358 the donation portion to the specific target organization defined within the temporal donation schedule (e.g., temporal donation schedule 78).

Concept #4

Figure 10:
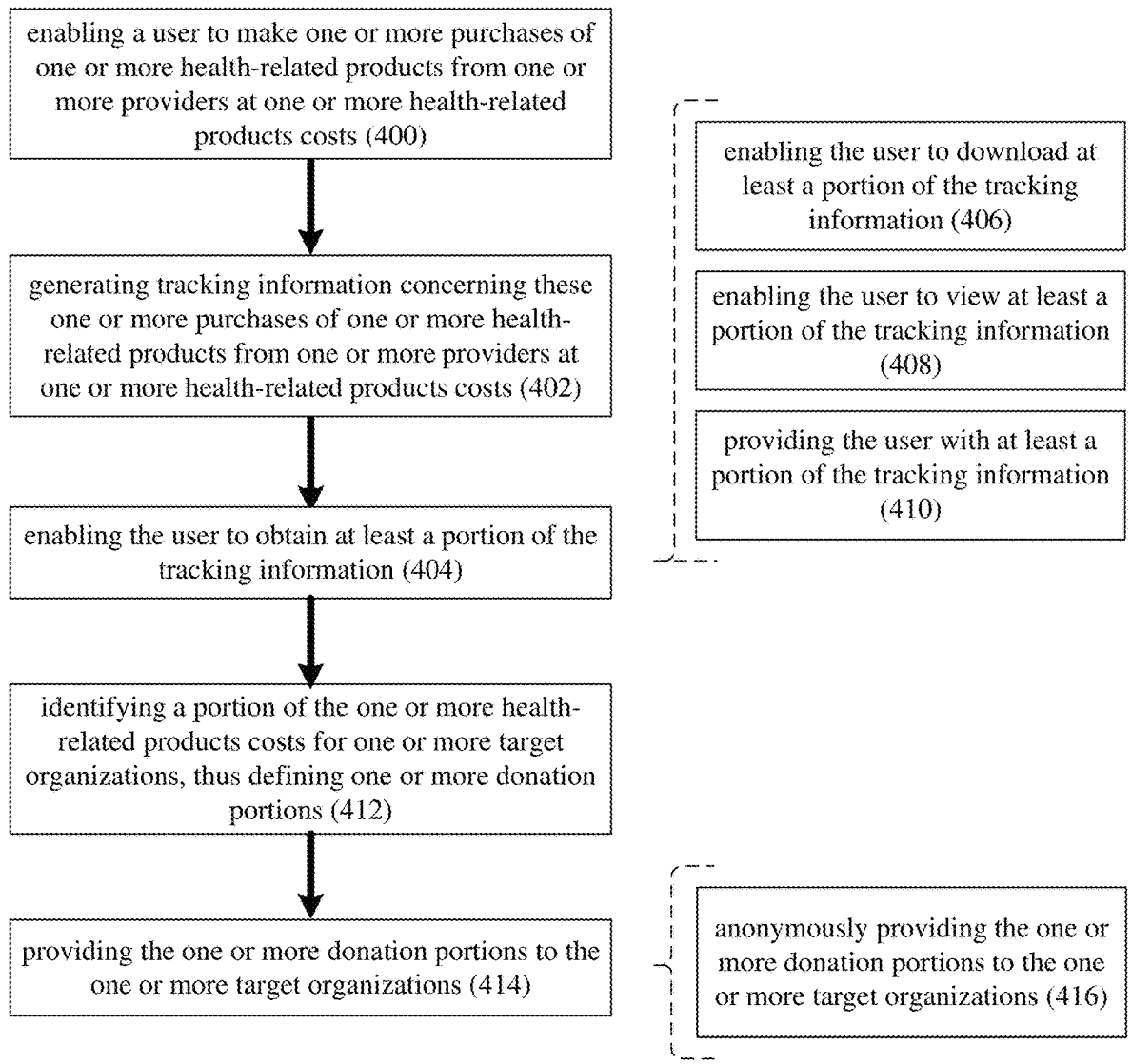
FIG. 10 is a flowchart of an implementation of the health-related product discount process of FIG. 1 according to an embodiment of the present disclosure.

As discussed above and referring also to FIG. 10, health-related product discount process 10 may enable 400 a user (e.g., user 36) to make one or more purchases of one or more health-related products (e.g., health-related product 58) from one or more providers (e.g., providers 60) at one or more health-related product costs. For example and over the course of e.g., a year, health-related product discount process 10 may enable 400 user 36 to make e.g., dozens of purchases of various health-related products (e.g., health-related product 58) from one or more of the providers (e.g., providers 60) at various health-related product costs.

Health-related product discount process 10 may generate 402 tracking information (e.g., tracking information 82) concerning these one or more purchases of one or more health-related products (e.g., health-related product 58) from one or more providers (e.g., providers 60) at one or more health-related product costs. Examples of this tracking information may include but is not limited to: usage information; purchase information; spend information; savings information; plan deductible information; donation information; and tax information.

Usage Information: Usage information may define the manner in which user 36 accessed and used health-related product discount process 10. For example, how often does user 36 use health-related product discount process 10 and what do they typically do within the system.

Purchase Information: Purchase information may define the specific purchases made by user 36 via health-related product discount process 10. For example, what specific health-related products (type, dosage, quantity) were made by user 36 using health-related product discount process 10.

Purchase Location Information: Purchase location information may define the specific purchase location(s) from which user 36 purchased health-related products using health-related product discount process 10.

Spend Information: Spend information may define the quantity of money spent on purchases made by user 36 via health-related product discount process 10. For example, what was the total amount of money spent by user 36 using health-related product discount process 10.

Savings Information: Savings information may define the quantity of money saved on purchases made by user 36 via health-related product discount process 10. For example, what was the total amount of money saved (versus full retail) by user 36 using health-related product discount process 10.

Plan Deductible Information; Plan deductible information may define the current levels of deductible for user 36. For example, how much more money will user 36 need to spend before getting out of the Medicare donut hole.

Donation Information: Donation information may define the quantity of donations made to target organizations (e.g., plurality of target organizations 80) in the name of user 36.

Tax Information: Tax information may define tax benefit information for donations made to target organizations (e.g., plurality of target organizations 80) in the name of user 36.

Due to the potential value of this tracking information (e.g., tracking information 82) for the user to which it pertains, health-related product discount process 10 may enable 404 the user (e.g., user 36) to obtain at least a portion of the tracking information (e.g., tracking information 82).

For example and when enabling 404 the user (e.g., user 36) to obtain at least a portion of the tracking information (e.g., tracking information 82), health-related product discount process 10 may enable 406 the user (e.g., user 36) to download at least a portion of the tracking information (e.g., tracking information 82). Accordingly, health-related product discount process 10 may be configured to enable 406 the user (e.g., user 36) to access a website (e.g., www.givebackrx.com) and download at least a portion of the tracking information (e.g., tracking information 82).

Further and when enabling 404 the user (e.g., user 36) to obtain at least a portion of the tracking information (e.g., tracking information 82), health-related product discount process 10 may enable 408 the user (e.g., user 36) to view at least a portion of the tracking information (e.g., tracking information 82). Accordingly, health-related product discount process 10 may be configured to enable 408 the user (e.g., user 36) to access a website (e.g., www.givebackrx.com) and view at least a portion of the tracking information (e.g., tracking information 82).

Additionally and when enabling 404 the user (e.g., user 36) to obtain at least a portion of the tracking information (e.g., tracking information 82), health-related product discount process 10 may provide 410 the user (e.g., user 36) with at least a portion of the tracking information (e.g., tracking information 82). Accordingly, health-related product discount process 10 may be configured to proactively provide 410 the user (e.g., user 36) with at least a portion of the tracking information (e.g., tracking information 82) at e.g., the end of a tax year.

As discussed above, health-related product discount process 10 may identify 412 a portion of the one or more health-related product costs for one or more target organizations (e.g., target organization 72), thus defining one or more donation portions (e.g., donation portion 74), wherein health-related product discount process 10 may provide 414 the one or more donation portions (e.g., donation portion 74) to the one or more target organizations (e.g., target organization 72).

In the manner described above with respect to user 36 being a registered user, a totally anonymous user or a charity-specific anonymous user, when providing 414 the one or more donation portions (e.g., donation portion 74) to the one or more target organizations (e.g., target organization 72), health-related product discount process 10 may anonymously provide 416 the one or more donation portions (e.g., donation portion 74) to the one or more target organizations (e.g., target organization 72).

GENERAL

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   receiving a query for a health-related product from a user;
   processing the query to identify providers from which the health-related product is available for purchase;
   generating a real-time geographic location of the user using a GPS chipset associated with the user;
   rendering a multi-item result set for the user on a user interface, wherein each item in the multi-item result set is associated with a provider name, a health-related product cost and a geographic proximity between the user and the provider, wherein rendering the multi-item result set for user includes rendering a map that visually locates each provider of each of the health-related product in the multi-item set with respect to the real-time geographic location of the user, wherein rendering the multi-item result set for the user includes rendering one or more items within the multi-item result set that have a lowest health-related product cost with a distinct icon adjacent to each of the one or more items, and wherein rendering the multi-item result set for the user includes rendering one or more items within the multi-item result set that have a best health-related product cost with a distinct text color compared to other items in the multi-item result set;
   identifying a portion of the health-related product cost for a target organization, thus defining a donation portion; and
   in response to determining that the user purchases the health-related product, providing the donation portion to the target organization.

2. The computer-implemented method of claim 1 further comprising:
   providing health-related product information to the user concerning the health-related product defined within the query.

3. The computer-implemented method of claim 1 further comprising:
   enabling the user to sort the multi-item result set based upon one or more of the provider name, the health-related product cost and the geographic proximity between the user and the provider.

4. The computer-implemented method of claim 1 further comprising:
   enabling the user to obtain a coupon to purchase the health-related product from a selected provider defined within the multi-item result set for the mediation cost associated with the selected provider.

5. The computer-implemented method of claim 1 wherein rendering a multi-item result set for the user includes:
presorting the items within the multi-item result set based upon geographic proximity between the user and the provider.

6. The computer-implemented method of claim 1 wherein rendering a multi-item result set for the user includes:
enabling the user to refine the multi-item result set based upon one or more of:
a health-related product name;
a health-related product form;
a health-related product dosage; and
a health-related product quantity.

7. A computer program product residing on a non-transitory computer readable medium having a plurality of instructions stored thereon which, when executed by a processor, cause the processor to perform operations comprising:
receiving a query for a health-related product from a user;
processing the query to identify providers from which the health-related product is available for purchase; and
generating a real-time geographic location of the user using a GPS chipset associated with the user;
rendering a multi-item result set for the user on a user interface, wherein each item in the multi-item result set is associated with a provider name, a health-related product cost and a geographic proximity between the user and the provider, wherein rendering the multi-item result set for user includes rendering a map that visually locates each provider of each of the health-related product in the multi-item set with respect to the real-time geographic location of the user, wherein rendering the multi-item result set for the user includes rendering one or more items within the multi-item result set that have a lowest health-related product cost with a distinct icon adjacent to each of the one or more items, and wherein rendering the multi-item result set for the user includes rendering one or more items within the multi-item result set that have a best health-related product cost with a distinct text color compared to other items in the multi-item result set;
identifying a portion of the health-related product cost for a target organization, thus defining a donation portion; and
in response to determining that the user purchases the health-related product, providing the donation portion to the target organization.

8. The computer program product of claim 7 further comprising:
providing health-related product information to the user concerning the health-related product defined within the query.

9. The computer program product of claim 7 further comprising:
enabling the user to sort the multi-item result set based upon one or more of the provider name, the health-related product cost and the geographic proximity between the user and the provider.

10. The computer program product of claim 7 further comprising:
enabling the user to obtain a coupon to purchase the health-related product from a selected provider defined within the multi-item result set for the mediation cost associated with the selected provider.

11. The computer program product of claim 7 wherein rendering a multi-item result set for the user includes:
presorting the items within the multi-item result set based upon geographic proximity between the user and the provider.

12. The computer program product of claim 7 wherein rendering a multi-item result set for the user includes:
enabling the user to refine the multi-item result set based upon one or more of:
a health-related product name;
a health-related product form;
a health-related product dosage; and
a health-related product quantity.

13. A computing system including a processor and memory configured to perform operations comprising:
receiving a query for a health-related product from a user;
processing the query to identify providers from which the health-related product is available for purchase; and
generating a real-time geographic location of the user using a GPS chipset associated with the user;
rendering a multi-item result set for the user on a user interface, wherein each item in the multi-item result set is associated with a provider name, a health-related product cost and a geographic proximity between the user and the provider, wherein rendering the multi-item result set for user includes rendering a map that visually locates each provider of each of the health-related product in the multi-item set with respect to the real-time geographic location of the user, wherein rendering the multi-item result set for the user includes rendering one or more items within the multi-item result set that have a lowest health-related product cost with a distinct icon adjacent to each of the one or more items, and wherein rendering the multi-item result set for the user includes rendering one or more items within the multi-item result set that have a best health-related product cost with a distinct text color compared to other items in the multi-item result set;
identifying a portion of the health-related product cost for a target organization, thus defining a donation portion; and
in response to determining that the user purchases the health-related product, providing the donation portion to the target organization.

14. The computing system of claim 13 further comprising:
providing health-related product information to the user concerning the health-related product defined within the query.

15. The computing system of claim 13 further comprising:
enabling the user to sort the multi-item result set based upon one or more of the provider name, the health-related product cost and the geographic proximity between the user and the provider.

16. The computing system of claim 13 further comprising:
enabling the user to obtain a coupon to purchase the health-related product from a selected provider defined within the multi-item result set for the mediation cost associated with the selected provider.

17. The computing system of claim 13 wherein rendering a multi-item result set for the user includes:
presorting the items within the multi-item result set based upon geographic proximity between the user and the provider.

18. The computing system of claim 13 wherein rendering a multi-item result set for the user includes:
   enabling the user to refine the multi-item result set based upon one or more of:
   a health-related product name;
   a health-related product form;
   a health-related product dosage; and
   a health-related product quantity.

* * * * *